United States Patent [19]
Lind

[11] 3,974,210
[45] Aug. 10, 1976

[54] ALKYLPHENOL DISULFONATES OF IMPROVED COLOR BY NEUTRALIZING WITH STRONG CAUSTIC

[75] Inventor: Wilton H. Lind, Petaluma, Calif.

[73] Assignee: Chevron Research Company, San Francisco, Calif.

[22] Filed: July 3, 1975

[21] Appl. No.: 592,907

Related U.S. Application Data

[63] Continuation of Ser. No. 285,715, Sept. 1, 1972, abandoned.

[52] U.S. Cl. .......... 260/512 R
[51] Int. Cl.[2] .......... C07C 143/42
[58] Field of Search .......... 260/512 R

[56] References Cited

UNITED STATES PATENTS

| | | | |
|---|---|---|---|
| 3,127,441 | 3/1964 | Valenta et al. | 260/512 R |
| 3,159,685 | 12/1964 | Bradley et al. | 260/619 |
| 3,766,254 | 10/1973 | Sharman et al. | 260/512 R |

*Primary Examiner*—James O. Thomas, Jr.
*Assistant Examiner*—Nicky Chan
*Attorney, Agent, or Firm*—G. F. Magdeburger; John Stoner, Jr.

[57] ABSTRACT

Alkylphenol disulfonates of improved color are provided by neutralizing alkylphenol disulfonic acid with aqueous solutions of alkali metal hydroxides having a base content of at least 30% by weight.

4 Claims, No Drawings

ALKYLPHENOL DISULFONATES OF IMPROVED COLOR BY NEUTRALIZING WITH STRONG CAUSTIC

This is a continuation of application Ser. No. 285,715, filed Sept. 1, 1972, now abandoned.

BACKGROUND OF THE INVENTION

Alkylphenol disulfonates have been found to be useful as heavy-duty, detergent-active materials. These materials have been prepared in the past by sulfonating alkylphenols in which the alkyl groups have from about 16 to 22 carbon atoms with a sulfonating agent such as oleum, sulfuric acid, chlorosulfonic acid, etc.; the sulfonating agent being employed in sufficient quantity to effect substantial ring disulfonation of the substituted phenol. The final material will contain an average of from about 1.5 to 2.0 sulfonic acid groups per molecule. In order to produce an effective heavy-duty detergent from the acidic material, it has been conventional to neutralize the disulfonic acid mixture with a water-soluble, salt-forming cation. It has been common to employ alkali metal and particularly sodium or potassium ions in the form of their oxides or hydroxides to neutralize the acids. In general, relatively weak solutions of the base (i.e., 10 to 25%) have been used, as the excess water was thought to aid in avoiding production of excessive temperatures in the reaction product which might have the effect of producing undesirable color in the product. In detergent production, it is important that color formation be avoided, as materials having low color (i.e., white or near white) are preferred by those using detergent powders, and the presence of excess color may cause coloring of the fabrics to be washed.

SUMMARY OF THE INVENTION

It has now been found, contrary to expectations, that when neutralizing alkylphenol disulfonic acid mixtures to produce disulfonates, the use of strong aqueous solutions of alkali metal hydroxides produces lower color levels than with conventional low weaker solutions. By strong solutions it is meant those containing over 30% by weight of base. Thus, strong solutions of base will contain from 30 up to about 50% by weight (the saturation level) of base.

DESCRIPTION OF THE PREFERRED EMBODIMENTS

The alkylphenol disulfonic acids and their salts are described in U.S. Patent Application Ser. No. 34,886, filed May 5, 1970 and now U.S. Pat. No. 3,766,254, granted Oct. 16, 1973. The preferred materials are derived from alkylphenols in which the alkyl group is substantially linear of 16 to 22 carbon atoms and not more than 25 mol percent of the materials have the alkyl groups positioned para to the phenolic hydroxy groups. The phenols are sulfonated with an appropriate sulfonating agent, oleum, chlorosulfonic acid, sulfuric acid, etc., until an average of at least 1.5 ring sulfonate groups per molecule are present. Since usually not more than two sulfonate groups will enter the ring, the products may be described as mixtures of mono- and disulfonates in which the disulfonates comprise at least half of the mixture. Additionally, for the purposes of effective detergency, the mixture contains 25 or less of para alkyl materials.

Applicants' improved process employs aqueous alkali metal hydroxides, particularly NaOH or KOH, in aqueous solutions having a concentration of at least 30% by weight of the hydroxide.

The following examples illustrate the process of this invention.

EXAMPLE 1

Preparation of Alkylphenol Disulfonic Acid

An alkylphenol in which the alkyl group was substantially linear having 17 to 20 carbon groups was fed at an average rate of 42 ml/min. to a continuous sulfonating unit along with 28 ml/min. of 20% oleum. The sulfonation was carried out at 125°F. and 20 psig with a residence time of about 10 minutes. The resultant product contained an average of 1.81 sulfonate groups per molecule. After digestion for 120 minutes at 85°F. and atmospheric pressure the product contained 1.87 sulfonate groups per molecule.

EXAMPLE 2

Neutralization of Alkylphenol Disulfonic Acid

The final product of Example 1 was divided into three portions; IA, IB, IC, and these were fed to a 700 ml continuous neutralizer at a rate of 50 ml/min. Aqueous solutions of NaOH were fed concurrently at rates required to produce a product with a pH of 7–9. Feed portion IA was neutralized at 100°F. and 20 psig by a 20% aqueous solution of NaOH; portion IB at 112°F. and 20 psig by a 30% NaOH solution; and portion IC at 160°F. and 20 psig by a 50% NaOH solution, the products being termed samples IIA, IIB and IIC respectively.

EXAMPLE 3

Determination of Color of Disodium Alkylphenol Disulfonate

The products of Example 2 (samples IIA, IIB, and IIC) were diluted to 5% concentrations in water and the color of each sample was measured in a 40-mm. cell in a Klett colorimeter. The results obtained are set forth in the following Table:

TABLE

Color of Disodium Alkylphenol Disulfonates

| SAMPLE | NaOH CONCENTRATION EMPLOYED IN NEUTRALIZING WEIGHT PERCENT | KLETT COLOR |
|---|---|---|
| IIA | 20 | 305 |
| IIB | 35 | 185 |
| IIC | 50 | 80 |

These data show that the color levels displayed by the salts formed by neutralizing the disulfonic acids with strongly basic solutions are surprisingly lower than when weaker basic solutions are used.

In effecting neutralization according to the processes of this invention, conventional techniques are employed. Thus, the basic solution may be added to a vessel containing the acidic, or vice versa, or the material may be intermixed in a circulating loop with the amount of base added being sufficient at least to neutralize the sulfonic acid and any additional inorganic acid, such as sulfuric, etc., which may be present in the acidic reaction mixture.

In some cases it may be desired that the pH of the detergent solution be either on the acidic or basic side, usually ranging anywhere from a pH of about 5 to 10. In such cases, a sufficient quantity of the base may be added to achieve the desired pH.

While the character of this invention has been described by specific examples, this has been done by way of illustration only and without limitation of the invention. It will be apparent to those skilled in the art that modifications and variations of the illustrative examples may be made in the practice of the invention within the scope of the following claims.

I claim:

1. A process for producing alkylphenol disulfonate based detergents of improved color which consists essentially of the steps of (1) sulfonating alkylphenol in which the alkyl group is substantially linear of 16 to 22 carbon atoms with a sulfonating agent until said product contains an average of from 1.5 to 2.0 sulfonic acid groups per molecule and (2) substantially neutralizing said product with an aqueous solution of an alkali metal hydroxide wherein the alkali metal hydroxide is present in the solution in an amount of at least 30% by weight.

2. The process of claim 1 in which the hydroxide is KOH or NaOH.

3. The process of claim 1 in which the hydroxide is NaOH.

4. The process of claim 1 in which the solution of alkali metal hydroxide has a concentration between 30% and saturation.

* * * * *